United States Patent [19]

Nakajima et al.

[11] Patent Number: 5,783,304
[45] Date of Patent: Jul. 21, 1998

[54] ACIDIC OR BASIC GAS ABSORPTIVE FIBER AND FABRIC

[75] Inventors: Shigeru Nakajima; Mitsuru Wakitani, both of Okayama, Japan

[73] Assignee: Japan Exlan Company Limited, Osaka, Japan

[21] Appl. No.: 796,815

[22] Filed: Feb. 6, 1997

[30] Foreign Application Priority Data

Feb. 26, 1996 [JP] Japan ................................. 8-065561

[51] Int. Cl.$^6$ ...................................... D02G 3/00
[52] U.S. Cl. ........................ 428/364; 428/395; 447/167
[58] Field of Search ................................. 428/364, 395; 525/329.1; 442/167

[56] References Cited

U.S. PATENT DOCUMENTS

| | | | |
|---|---|---|---|
| 5,109,028 | 4/1992 | Tanaka et al. | 521/32 |
| 5,292,822 | 3/1994 | Tanaka et al. | 525/329.1 |

FOREIGN PATENT DOCUMENTS

| | | |
|---|---|---|
| 0722004 | 7/1996 | European Pat. Off. . |
| 49-59091 | 6/1974 | Japan . |
| 63-75041 | 4/1988 | Japan . |
| 2-84528 | 3/1990 | Japan . |
| 2194752 | 3/1988 | United Kingdom . |

OTHER PUBLICATIONS

Database WPI, Section Ch, Week 9623, Derwent Publications Ltd., London, GB; Class A14, AN 96-228776 XP002046957 & RU 2 044 748 C (Khimvolokno Sci Prodn Assoc), Sep. 27, 1995.

Database WPI, Section Ch, Derwent Publications Ltd., London, GB; Class A14, AN 72-73385T XP002019467 & SU 332 148 A (Dorokhina Is Zverev MP BA).

Primary Examiner—Newton Edwards
Attorney, Agent, or Firm—Wenderoth, Lind & Ponack, L.L.P.

[57] ABSTRACT

Disclosed are acidic or basic gas absorptive fiber having both a degree of acidic gas absorption of 70% or higher and a degree of basic gas absorption of 80% or higher, and also fabric comprising the fiber. The fiber and fabric, after having absorbed acidic and basic gases, can easily be restored to its original condition if they are exposed to clean air. The fiber is preferably crosslinked acrylic fiber, which has a specific increase in its nitrogen content resulting from crosslinking with hydrazine, a specific amount of carboxyl groups resulting from modification with nitrile groups, a specific ratio of free carboxyl groups to all carboxyl groups existing therein, and a specific equilibrated pH in water, and which is prepared from acrylic fiber through crosslinking with hydrazine, hydrolysis, and conversion of carboxyl groups therein into metal carboxylate groups. The fiber and fabric are durable to cycle use.

12 Claims, No Drawings

ACIDIC OR BASIC GAS ABSORPTIVE FIBER AND FABRIC

TECHNICAL FIELD

The present invention relates to acidic or basic gas absorptive fiber and fabric capable of reversibly absorbing and releasing acidic and basic gases, of which the gas absorption rate is great and which are durable to cycle use.

FIELD OF THE INVENTION

With the recent change in living styles that includes the increase in the density and the degree of airtightness in recent living environments, offensive odors have become problematic, and there is a great demand for the removal of odors. Above all, acidic gas of, for example, acetic acid, and basic gas of, for example, ammonia and trimethylamine are said to be typical gasses that give offensive odors, along with gas of hydrogen sulfide and methylmercaptan.

As deodorizing fibers, for example, known are fibers having a deodorizing substance as adhered and fixed onto their surfaces, and activated carbon fibers. However, the former are problematic in their durability and feel, while the latter are also problematic in their costs and deodorizability for ammonia and are additionally defective in that they require high temperatures for regeneration and especially require chemicals for chemical regeneration. As gas absorptive fibers capable of absorbing either basic gas or acidic gas, known are ones that utilize the deodorizing mechanism of neutralization of themselves. However, there is known no fiber capable of absorbing both acidic gas and basic gas of which the properties are contradictory to each other. Basically, the conventional fibers with a substance as adhered thereto through any post-treatment of the fibers to participate in the neutralization thereof do not have great deodorizing ability. As one means of introducing functional groups into fiber, known is a method of introducing carboxyl groups into acrylic fiber, in which, however, the number of the functional groups to be in the resulting fiber is increased with the result that the physical properties of the fiber are worsened. At present, therefore, there is known no fiber having great deodorizing ability while having good mechanical and physical properties.

SUMMARY OF THE INVENTION

The object of the present invention is to provide acidic or basic gas absorptive fiber and fabric capable of absorbing large amounts of both acidic gas and basic gas, of which the properties are contradictory to each other, at a great rate of absorption. The fiber and fabric of the invention are advantageous in that they can be handled with ease, that they have good mechanical and physical properties in such a degree that they can be processed and worked into any desired shapes, and that they can be regenerated with ease.

In order to attain the above-mentioned object, the present inventors have assiduously studied and have completed the present invention. Specifically, the present invention provides acidic or basic gas absorptive fiber having both a degree of acidic gas absorption of 70% or higher and a degree of basic gas absorption of 80% or higher. Preferably, the fiber of the invention is crosslinked acrylic fiber, of which the increase in the nitrogen content resulting from hydrazine crosslinking therein falls between 1.0 and 8.0% by weight, which has from 2.5 to 6.0 mmol/g, preferably from 3.0 to 6.0 mmol/g of carboxyl groups as introduced into a part of the remaining nitrile groups while having amido groups as introduced into the remaining part thereof, and in which a part of said carboxyl groups are of salt types with one or more metals selected from K, Na, Ca, Mg and Al while the proportion of the amount of free carboxyl groups to the amount of all said carboxyl groups falls between 30 and 95 mol %, preferably between 40 and 90 mol %.

Further preferably, the acidic or basic gas absorptive fiber of the present invention has, when dispersed in water in an amount of one gram per 500 ml of water, an equilibrated pH of from 5.0 to 8.0, which produces better results. The present invention also includes acidic or basic gas absorptive fabric comprising said acidic or basic gas absorptive fiber in an amount of 5% by weight or more. The degree of acidic gas absorption and the degree of basic gas absorption as referred to herein for the fiber and fabric of the invention are defined by the following test method I and test method II, respectively.

Test Method I

One gram of a fiber sample as dried absolutely at 105° C. is left in a standard atmosphere at 20° C. and at 65% RH for 10 hours or longer, then airtightly sealed in a Tedlar® bag along with 1000 ml of a mixed gas comprising air and having an acetic acid concentration of 50 ppm, and left therein at 20° C. for 2 hours; and the acetic acid concentration in the mixed gas in the bag is measured, from which is obtained the decrease in acetic acid gas therein that indicates the degree of acidic gas absorption of the fiber sample.

Test Method II

One gram of a fiber sample as dried absolutely at 105° C. is left in a standard atmosphere at 20° C. and at 65% RH for 10 hours or longer, then airtightly sealed in a Tedlar® bag along with 1000 ml of a mixed gas comprising air and having an ammonia concentration of 100 ppm, and left therein at 20° C. for 2 hours; and the ammonia concentration in the mixed gas in the bag is measured, from which is obtained the decrease in ammonia gas therein that indicates the degree of basic gas absorption of the fiber sample.

DETAILED DESCRIPTION OF THE INVENTION

Now, the present invention is described in detail hereinunder. The acid or basic gas absorptive fiber of the present invention has both a degree of acidic gas absorption as measured according to the test method I of 70% or higher, preferably 80% or higher, and a degree of basic gas absorption as measured according to the test method II of 80% or higher, preferably 90% or higher. If the degrees of gas absorption of the fiber are lower than the defined ranges, such is unfavorable for practical use of the fiber since the acidic and basic gas concentrations remaining in the fiber are high.

Preferably, the fiber of the invention is crosslinked acrylic fiber that starts from acrylic fiber made from an acrylonitrile (hereinafter referred to as AN) polymer having an AN content of 40% by weight or higher, desirably 50% by weight or higher. The fiber may be of any form of, for example, short fiber, tow, knitted or woven fabric, and non-woven fabric, and it may even be a half-finished one obtainable halfway in fiber production, waste fiber or the like. The AN polymer may be any of AN homopolymers and AN copolymers comprising AN and other comonomers. The comonomers include, for example, vinyl halides and vinylidene halides; (meth)acrylates [the expression (meth)

as referred to herein is meant to include both meth-free compounds and meth-added compounds]; sulfonic acid group-containing monomers, such as methallylsulfonic acid and p-styrenesulfonic acid, and their salts; carboxyl acid group-containing monomers, such as (meth)acrylic acid and itaconic acid, and their salts; and other monomers such as acrylamide, styrene and vinyl acetate. The means of producing the starting acrylic fiber is not specifically limited but may be any known one.

To introduce hydrazine crosslinking structure into the acrylic fiber, employable is any means of controlling the increase in the nitrogen content of the fiber to fall between 1.0 and 8.0% by weight. Industrially, however, preferred is a means of processing the fiber at a temperature of from 50° to 130° C., preferably from 85° to 130° C., for from 1 to 8 hours, preferably from 1 to 4 hours, to thereby make the fiber have a hydrazine concentration of from 3 to 80% by weight, preferably from 5 to 40% by weight. The increase in the nitrogen content of the fiber as referred to herein indicates the difference between the nitrogen content of the starting acrylic fiber and that of the hydrazine-crosslinked acrylic fiber.

If the increase in the nitrogen content in question is below the lowermost limit of the defined range, the final fiber to be obtained herein could not have satisfactory physical properties on a practicable level, resulting in failure in attaining the object of the invention. On the other hand, if it is above the uppermost limit, the final fiber could not have the ability to satisfactorily absorb acidic and basic gases, also resulting in failure in attaining the object of the invention. The conditions necessary for the increase in the nitrogen content in question, which is specifically defined herein to fall between 1.0 and 8.0% by weight, can be easily determined by clarifying the relationship between the reaction factors, such as reaction temperature, concentration of reactants and reaction time, and the increase in the nitrogen content of the fiber obtained, through experiments. The hydrazine employable herein includes, for example, hydrazine hydrate, hydrazine sulfate, hydrazine hydrochloride, hydrazine nitrate and hydrazine hydrobromide.

To substantially remove the nitrile groups as remaining in the fiber without being crosslinked with hydrazine, through hydrolysis thereby to finally introduce into the fiber carboxyl groups of from 2.5 to 6.0 mmol/g along with amido groups of the balance, employable is a means of dipping the starting fiber in an aqueous solution of a basic substance such as alkali metal hydroxide or ammonia or in an aqueous solution of a mineral acid such as nitric acid, sulfuric acid or hydrochloric acid, or a means of dipping it in such an aqueous solution under heat. If desired, the starting fiber may be hydrolyzed along with the introduction of the crosslinking bonds thereinto. If, however, the carboxyl group content of the final fiber is below the lowermost limit of the defined range, the fiber could not have the practical ability to satisfactorily absorb acidic and basic gases. If, on the other hand, it is above the uppermost limit, the fiber could not have satisfactory physical properties on a practicable level. The conditions necessary for controlling the carboxyl group content of the fiber of the invention to fall between 2.5 and 6.0 mmol/g can be easily determined by clarifying the relationship between the reaction factors, such as reaction temperature, concentration of reactants and reaction time, and the amount of the carboxyl groups to be introduced into the fiber, through experiments.

The thus-introduced carboxyl groups shall consist essentially of their salts of at least one or more metals selected from K, Na, Ca, Mg and Al and free carboxyl groups of from 30 to 95 mol % relative to the amount of all carboxyl groups existing in the fiber. For this purpose, for example, employable is a method of controlling the pH of the fiber to fall between 4.0 and 7.0 by adding to the fiber at least one or more hydroxides with one or more metals selected from K, Na, Ca, Mg and Al, when the fiber was hydrolyzed with an acid; or a method of controlling the pH of the fiber to fall between 4.0 and 7.0 by adding to the fiber at least one or more acids selected from sulfuric acid, hydrochloric acid, nitric acid and phosphoric acid, to thereby convert a part of the carboxyl groups in the fiber into acid-type ones, when the fiber was hydrolyzed with an alkali. In particular, if one or more divalent metal salts are introduced into the fiber, preferably employed is a method in which a part of the carboxyl groups in the fiber are converted into salt-type ones with K and/or Na and thereafter one or more metal salts selected from nitrates, hydrochlorides and phosphates with Ca, Mg and Al are added to the fiber to thereby convert a part of the carboxyl groups in the fiber into their metal salts. This method is especially preferred since the fine structure of the fiber being processed by this can be semi-swollen and the conversion of the carboxyl groups into their metal salts can be conducted rapidly and uniformly to the depth of the fiber. The fiber thus processed to have the metal salts therein is then washed with water, finished with oil and dried.

If the free carboxyl group content of the fiber is below the lowermost limit of the defined range, the ability of the fiber to absorb basic gas is small, and the gas-absorbing rate of the fiber is also small. If, however, it is above the uppermost limit, the ability of the fiber to absorb acidic gas is small, and the gas-absorbing rate of the fiber is also small. Since the fiber of the present invention is characterized in that it can absorb a plurality of gases, of which the properties are contradictory to each other, that the amount of gas absorption of the fiber is large and that the gas-absorbing rate of the fiber is great, the proportion of the free hydroxyl groups to the metal carboxylate groups in the fiber is an especially important factor. Further, as mentioned in detail hereinunder, the fiber to be provided by the present invention can be easily regenerated. Specifically, since the acid or basic gas absorption to be attained by the fiber of the invention is a reversible reaction and since the amount of gas to be absorbed by the fiber of a unit amount is determined depending on the acid or basic gas concentration in the ambient atmosphere, the acidic and basic gases as once absorbed by the fiber can be released therefrom after the fiber is exposed to clean air whereby the gas-absorbing ability of the fiber can be easily regenerated or, that is, the fiber is easily restored to its original condition.

Metal carboxylates other than carboxylates with K, Na, Ca, Mg and Al, if being in fiber, are ineffective for absorbing acidic and basic gases or will be harmful to humans, and these are not always recommended to be in the fiber of the invention. In the fiber of the present invention, however, the presence of any other metals to be derived from any particular methods for fiber production is not prohibited, but the metal content shall be at most up to 0.4 mmol/g or lower in terms of the metal carboxylates.

In order to make the fiber of the present invention have an especially high tensile strength, it is desirable to select acrylic fiber having a high dichroism ratio as the starting fiber, as will be described in detail hereinunder.

As the means of attaining the present invention, preferably employed is an apparatus comprising a reaction tank equipped with a pump-circulation system, in which starting acrylic fiber is put into the reactor, the intended crosslinking structure is introduced into the fiber, and the fiber is hydrolyzed and processed to thereby form metal salts therein in that order, since the apparatus is safe and the process can attain uniform reactions. One typical example of the apparatus of this type (comprising a reaction tank equipped with a pump-circulation system) is a pressure reactor.

In order that the present invention may provide the intended acid or basic gas absorptive fiber having practicable physical properties and a high degree of acid or basic gas absorbing ability, it is especially desirable to employ, as the starting fiber, acrylic fiber having the following characteristics.

Specifically, the starting fiber is desirably acrylic fiber of an AN polymer such that the polymer molecules constituting the fiber are well oriented and that the dichroism ratio with Congo Red (hereinafter referred to as CR) of the fiber 0.4 or more, preferably 0.5 or more. The CR dichroism ratio can be obtained according to the method described in Polymer Chemistry, 23 (252), 193 (1966).

The means of producing the acrylic fiber of this type is not specifically defined, and any known means is employable so far as the fiber produced may satisfy the above-defined CR dichroism ratio. In particular, however, preferably employed is an industrial means of attaining a degree of total stretching of fiber of 4 times or higher, preferably 8 times or higher, and attaining a degree of shrinkage of fiber in its production process of 40% or lower, preferably 30% or lower, by which the intended acrylic fiber can be produced advantageously.

It is especially desirable to employ, as the starting fiber, stretched but not heat-treated acrylic fiber (this is fiber as obtained by spinning a spinning stock of an AN polymer in an ordinary manner, and this is stretched and oriented but is not subjected to heat treatment, such as dry heat densification treatment or wet heat relaxation treatment; above all, this is water-swollen, gel-like fiber after wet or dry/wet spinning followed by stretching, having a degree of water-swelling of from 30 to 150%). The starting acrylic fiber of this type has high dispersibility in reaction liquid and, in addition, the penetration of reaction liquid into the fiber is attained rapidly. Therefore, the introduction of crosslinking bonds into the fiber and the hydrolysis of the fiber can be attained uniformly and rapidly. Needless-to-say, the degree of water-swelling as referred to herein indicates a percentage of the water content of fiber as expressed relative to the weight of dry fiber.

The fiber of the present invention is characterized in that it can absorb a plurality of gases, of which the properties are contradictory to each other, that the amount of gas absorption of the fiber is large and that the gas-absorbing rate of the fiber is great. Accordingly, the ratio of the amount of free carboxyl groups to that of all carboxyl groups in the fiber, and also the equilibrated pH value of the fiber as dispersed in water in a amount of one gram per 500 ml of water are important factors in the present invention. The equilibrated pH value shall fall between 5.0 and 8.0, preferably between 5.5 and 8.0. If it is below or above the defined range, the fiber could not absorb a plurality of gases, of which the properties are contradictory to each other, unfavorably resulting in that not only the gas-absorbing ability of the fiber is one-sided but also the color fastness of the fiber is lowered and additionally the dyed fiber is discolored. In addition, if the equilibrated pH value of the fiber is outside the defined range, such is unfavorable since the fiber, if kept in direct contact with the skin, may often roughen the skin. Since the fiber of the present invention has both salt-type carboxyl groups (carboxylate groups) and acid-type carboxyl groups (free carboxyl groups) as introduced thereinto, it has a pH-buffering action, or that is, the ability to maintain its pH value to fall within the range between a neutral one and a weakly acidic one, which is said to be good to the skin. Such a pH-buffering action of the fiber of the invention is specifically referred to herein as a remarkable effect of the fiber.

The conditions for attaining the equilibrated pH value of the fiber of from 5.0 to 8.0 may vary, depending on the ratio of the amount of free carboxyl groups to that of all carboxyl groups in the fiber and even on the type of the carboxylate groups therein, but can be easily determined by clarifying the relationship between the reaction factors, such as the reaction pH during metal salt treatment, the concentration of reactants and the reaction time for the treatment, and the value of the equilibrated pH of the fiber, through experiments.

The acidic gas as referred to herein may include gases of acidic compounds of, for example, organic acids such as formic acid, acetic acid, propionic acid, butyric acid and valeric acid, and inorganic acids, while the basic gas may include gases of basic compounds of, for example, amines such as methylamine, ethylamine, propylamine, diethylamine, trimethylamine, triethylamine, and ammonia.

The present invention includes acid or basic gas absorptive fabric that partly comprises the acid or basic gas absorptive fiber of the invention in an amount of 5% by weight or more. The outward appearance of the fabric of the invention may include any of threads, yarns (including lap yarns), filaments, woven fabrics, knitted fabrics, non-woven fabrics, paper-like fabrics, sheets, laminates and floccules (including spherical and bulky ones), which may be covered with outer coats. Regarding the form of the fiber of the invention to be in the fabric, the fiber may be mixed with other material and formed into fabric containing the fiber substantially uniformly therein. If the fabric comprises a plurality of layers, the fiber may be localized in any one or more layers or may be distributed in all layers at a predetermined ratio.

Accordingly, the fabric of the present invention includes innumerable varieties of combinations of its outward appearance and the form of the fiber to be in the fabric, such as those mentioned hereinabove. Therefore, since the fiber of the present invention has many functions such as those mentioned hereinabove, the final fabric of the invention may be suitably determined in consideration of, for example, the mode of its use (for example, considering when it is used in what season; considering its fitness for exercise; considering how it is used in inner wear, outer wear, or wear to be put between inner wear and outer wear; considering its use as curtains, carpets, bedding, cushions, or insoles; and considering its use in air conditioners), its necessary functions, and the mode how the fiber of the invention acts to express its functions.

Referring in detail to the structure of the fabric of the invention, it includes uniform mixtures as prepared by merely mixing only the fibers of the invention or by merely mixing the fibers of the invention and other materials, and laminates of from 2 to 5 layers as prepared by attaching layers of other materials to layers of such mixtures or sandwiching layers of other materials between layers of such mixtures, for example, via an adhesive therebetween or by heat-sealing them, followed by integrating them.

It may further include laminates supported by a support, in which the constituent layers are not positively integrated.

The use of the final product comprising the fabric of the invention is broad, as mentioned hereinabove. For example, the fabric can be used as wear for human beings, in bedding such as bed kilts, pillows and cushions, in interior decorations such as typically curtains and carpets, and even in other various fields for air-conditioning and deodorization.

Therefore, depending on the use of the fabric, prepared are single-layered structures or multi-layered laminate structures comprising the fabric, which may be further covered with any other coats, in order that the fabric may satisfactorily exhibit the intended functions in these products.

The fabric of the present invention comprises the acid or basic gas absorptive fiber of the invention in an amount of 5% by weight or more. Therefore, it may comprise any other materials, such as fibers, rubbers, resins and plastics, in an amount of 95% by weight of its total weight. If the fabric is made of only the fiber of the invention, i.e. 100% by weight the fiber of the invention, it does not comprise any other material. In general, where the fabric of the invention is made of a mixture comprising the fiber of the invention and other materials, the amount of the fiber of the invention in the fabric is 5% by weight or more, preferably 10% by weight or more. If it is less than 5% by weight, the fabric, even though comprising the fiber of the invention, could not satisfactorily express the favorable functions of the fiber.

The combination of the fiber of the invention and other materials to construct the fabric of the invention is preferred, as further improving the functions of the fabric. Although the fiber of the invention has various favorable functions such as those mentioned hereinabove, it is preferably formed into more fashionable fabrics having much more improved functions, feel and dyeability in vivid color. In addition, where the fiber of the invention is blended with any other different fibers, the processability and the workability of the resulting blend may be much improved.

Other fibers to be combined with the fiber of the invention to form fabric are not limited at all but may be any ordinary ones, including, for example, natural fiber, semi-synthetic fiber, synthetic fiber, and even inorganic fiber and glass fiber, if acceptable. The materials to be combined with the fiber or fabric of the invention are not limited to only fibers but maybe any others. As mentioned hereinabove, the fabric may be laminated with film; or the fiber may be embedded in film to form fabric. Thus, plastics and rubber materials are also employable herein. Especially preferred examples of other fibers capable of being combined with the fiber of the invention include natural fiber of, for example, wool or cotton; synthetic fiber such as polyester, polyamide or polyacrylic fiber; and even rayon and polynosic fiber.

The fabric comprising the fiber of the invention in an amount of 5% by weight or more can satisfactorily express the functions of the fiber owing to the synergistic effect of the fiber of the invention and the other materials as combined therewith, even though the content of the fiber of the invention in the fabric is small. Further, the fabric of the invention, as being made of the combination of the fiber of the invention and other materials, may have additional functions. Thus, the present invention can provide a variety of final products with various functions.

One popular embodiment of fabric is non-woven fabric. Where the fiber of the invention is formed into such non-woven fabric, it is desirable that the fiber is short fiber and is blended with any other materials of, for example, cellulosic fiber, pulp and synthetic fiber. In particular, recommended is non-woven fabric for use that requires high dimensional stability, which comprises the fiber of the invention and heat-adhesive fiber and in which the proportion of the fiber of the invention is preferably from 5 to 80% by weight. The heat-adhesive fiber employable herein may be any one exhibiting adhesiveness under heat, and may include, for example, mixed fibers composed of a low-melting-point component and a high-melting-point component, such as polyethylene-polypropylene fiber, polyethylene-polyester fiber and polyester-polyester fiber. The non-woven fabric comprising the fiber of the invention is, when kept in contact with human bodies, good to the skin, while having water absorbability, and therefore is suitable in use where the fabric shall exhibit its acidic or basic gas absorbing ability.

For example, the non-woven fabric comprising the fiber of the invention is suitable in use for diapers and pads for incontinence. It can be used as not only the top sheet but also the back sheet of these. Using the non-woven fabric in diapers or pads, therefore, the amount of high water-absorbing polymer in these can be reduced. In addition, since the fiber of the present invention has high water-absorbability and has a microbicidal property, wear made of the fabric comprising the fiber is further advantageous in that the wearer does not feel stuffy and his/her skin is not roughened by it, even though wearing it for a long period of time. In order to more effectively utilize the characteristics of the fiber of the present invention, it is desirable that the fiber is in fabric on its side that is to be exposed to acidic and basic gases.

The reason why the acidic or basic gas absorptive fiber of the present invention has such a high degree of acidic or basic gas absorbability, while having good physical properties, is not as yet completely clarified, but may be considered to be as follows.

Although the fiber of the present invention starts from an AN polymer, it may have substantially no nitrile group therein. In the fiber of this type, therefore, the side chains bonding to each polymer chain may comprise nitrogen-containing, crosslinking structures as formed through the reaction with hydrazine, and free carboxyl groups, metal carboxylate groups and amido groups as formed through the hydrolysis of nitrile groups. Accordingly, the reason why the fiber of the invention absorbs acidic and basic gases will be because basic gas may be reacted with the free carboxyl groups existing in the fiber through acid-base reaction therebetween while acidic gas may be reacted with the metal carboxylate groups existing therein also through acid-base reaction therebetween. Since the acid-base reaction is a reversible reaction, the gas-absorbing ability of the fiber can be easily regenerated or, that is, the fiber can be easily restored to its original condition. As mentioned above, the fiber of the invention has a high degree of acidic or basic gas absorbability, while having good physical properties. This may be considered because, as having crosslinking structures therein, the fiber may still maintain its own yarn-forming property even after the nitrile groups therein, which are indispensable for the yarn-forming property of acrylic fiber, are converted into carboxyl groups.

In addition to the acidic or basic gas absorbing ability, the fiber of the invention has good processability and workability, which will be significantly derived from its oriented structure that may be verified by its CR dichroism ratio, and from the intramolecular and intermolecular ionic-crosslinking with the poly-valent metals existing therein.

Though having such a high degree of acidic or basic gas absorbing ability, the fiber of the present invention, after having absorbed large amounts of acidic and basic gases, may be easily restored to its original condition. As has been mentioned hereinabove, the fiber of the invention, after having once absorbed acidic and basic gases, can release the gases therefrom if it is exposed to clean air, resulting in that the gas-absorbing ability of the fiber can be easily regenerated or, that is, the fiber can be easily restored to its original condition. In order to further facilitate the regeneration or restoration of the fiber, any additional means may be employed herein. For example, where the basic gas absorbability of the fiber is desired to be recovered to its original one, the fiber may be treated with a weak acid, such as acetic acid or formic acid, or with a diluted inorganic acid and thereafter may be washed with water; and where the acidic gas absorbability of the fiber is desired to be recovered to its original one, the fiber may be treated with aqueous ammonia or with a diluted alkaline solution and thereafter may be washed with water.

Now, the present invention is described concretely hereinunder with reference to the following examples, in which parts and percentages are by weight unless otherwise specifically indicated.

The acidic or basic gas absorbability of fiber samples, the amount of all carboxyl groups in fiber samples, the amount of metal carboxylate groups therein (meq/g), the amount of free carboxyl groups therein (meq/g), the pH-buffering ability of fiber samples (µeq/g), and the pH of fiber samples dipped in water, all referred to in the following examples, were obtained according to the methods mentioned below. All gas absorbing tests were carried out in atmosphere (at 1 atm).

(1) Amount of All Carboxyl Groups (meq/g)

About 1 g of a fiber sample that had been fully dried was weighed to be (X) g, to which was added 200 ml of an aqueous solution of 1N hydrochloric acid. After having been left as it was for 30 minutes, the resulting mixture was filtered through a glass filter, and then washed with water added thereto. This treatment with hydrochloric acid was repeated three times. Then, the fiber sample was fully washed with water until the pH of the filtrate resulting from the filtration of the fiber sample became 5 or higher. Next, this sample was put into 200 ml of water, which was then made to have a pH of 2 with an aqueous solution of 1N hydrochloric acid added thereto. Next, the titration curve of the sample was obtained according to an ordinary method using an aqueous solution of 0.1N sodium hydroxide. From the titration curve, obtained was the amount (Y ml) of the aqueous solution of sodium hydroxide as consumed by the carboxyl groups existing in the fiber sample. From this was obtained the amount of the carboxyl groups existing in the fiber sample, according to the following equation.

*Amount of All Carboxyl Groups (meq/g)=0.1 Y/X*

(2) Amount of Free Carboxyl Groups (meq/g)

About 1 g of a fiber sample that had been fully dried was weighed to be (X) g, to which were added 200 ml of water and (Z1) ml of an aqueous solution of 0.1N sodium hydroxide that was equivalent to the amount of all carboxyl groups existing in the sample. The resulting mixture was stirred for 1 hour, and then filtered through a glass filter to separate the fiber. Then, the resulting filtrate was titered through neutralization with an aqueous solution of 0.1N hydrochloric acid, using phenolphthalein as the indicator. The amount (Z2 ml) of the aqueous solution of hydrochloric acid as consumed for the neutralization was obtained, from which was obtained the amount of free carboxyl groups that had existed in the sample, according to the following equation.

*Amount of Free Carboxyl Groups (meq/g)=[0.1 (Z1−Z2)]/X*

(3) Basic Gas Absorbability

One gram of a fiber sample that had been absolutely dried at 105° C. was conditioned in a standard atmosphere at 20° C. and at 65% RH for 10 hours or longer. The thus-conditioned fiber sample was put into a Tedlar® bag and sealed therein, into which was introduced basic gas to reach a predetermined concentration. Then, the sample was left as it was under the condition for 2 hours at 20° C., and thereafter the gas concentration in the bag was measured with a gas detector. From the thus-measured gas concentration as remained in the bag and the initial gas concentration as had been therein, obtained was the reduction in the basic gas in the bag.

(4) Acidic Gas Absorbability

One gram of a fiber sample that had been absolutely dried at 105° C. was conditioned in a standard atmosphere at 20° C. and at 65% RH for 10 hours or longer. The thus-conditioned fiber sample was put into a Tedlar® bag and sealed therein, into which was introduced acidic gas to reach a predetermined concentration. Then, the sample was left as it was under the condition for 2 hours at 20° C., and thereafter the gas concentration in the bag was measured with a gas detector. From the thus-measured gas concentration as remained in the bag and the initial gas concentration as had been therein, obtained was the reduction in the acidic gas in the bag.

(5) pH-buffering Ability (µeq/g)

About 0.4 g of a fiber sample that had been absolutely dried at 105° C. was weighed to be (X) g, to which was added 200 ml of water. Then, an aqueous solution of 0.1N hydrochloric acid or an aqueous solution of 0.1N sodium hydroxide was dropwise added thereto to reach pH of 5.0 for the former or pH of 7.0 for the latter, whereupon the amount (Y ml) of the aqueous solution of hydrochloric acid or the aqueous solution of sodium hydroxide consumed was obtained. From the data, obtained was the pH-buffering ability of the fiber sample for the acid or alkali according to the following equation.

*pH-buffering Ability (µeq/g)=1000 Y/X*

(6) pH of Fiber Dipped in Water

One gram of a fiber sample that had been fully dried was weighed, to which was added 500 ml of water. Then, this was stirred and dispersed at 20° C. for 1 hour, whereupon the equilibrated pH value of the resulting fiber dispersion was measured.

EXAMPLE 1

12 parts of an AN polymer composed of 90% of AN and 10% of methyl acrylate (hereinafter referred to as MA) (the polymer had a limiting viscosity [h] of 1.5 in dimethylformamide at 30° C.) was dissolved in 88 parts of an aqueous solution of 48% sodium rhodanide to prepare a spinning stock. This was spun and stretched (at a total stretching magnification of 10 times) in an ordinary manner, then dried in an atmosphere at dry-bulb temperature/wet-bulb temperature=120° C./60° C., thereafter relaxed in high-pressure steam at 125° C. (to a degree of shrinkage in process of 30%), and finally crimped to give raw fiber having a single fiber fineness of 1.0 d (and having a CR dichroism ratio of 0.56).

The raw fiber prepared above was subjected to hydrazine crosslinking treatment and hydrolyzed under the conditions as shown in Table 1 below, then dipped in an aqueous solution of 1N nitric acid for 30 minutes, and washed with water. The increase in the weight of the fiber after the crosslinking, and the amount of carboxyl groups existing in the fiber after the hydrolysis were measured and shown in Table 2 below. Next, these fiber samples were processed for pH control under the condition as shown in Table 1 to obtain modified fiber samples where a part of carboxyl groups existing therein were converted into mono-valent metal carboxylate groups.

Sample Nos. 1 to 3 of the invention and comparative sample Nos. 6 and 7 were then processed with any of metal salts under the condition shown in Table 1. After having been fully washed with water, these were dried. Thus were obtained herein sample Nos. 1 to 9 as in Table 1. The characteristic values and the degrees of acidic or basic gas absorbing ability of these samples are shown in Table 2.

TABLE 1

| Example | Fiber Sample No. | Hydrazine Treatment | | | Hydrolysis | | | | pH Control Treatment | | Metal Salt Treatment | | |
|---|---|---|---|---|---|---|---|---|---|---|---|---|---|
| | | % | °C. | Hrs | Chemical | % | °C. | Hrs | Chemical | pH | Metal Salt | °C. | Hrs |
| Sample of the Invention | 1 | 35 | 98 | 2 | NaOH | 10 | 90 | 2 | NaOH | 5.5 | Ca(NO$_3$)$_2$ | 60 | 2 |
| Sample of the Invention | 2 | 10 | 120 | 3 | NaOH | 10 | 90 | 2 | NaOH | 4.5 | Ca(NO$_3$)$_2$ | 60 | 2 |
| Sample of the Invention | 3 | 5 | 125 | 5 | NaOH | 10 | 90 | 2 | NaOH | 5.5 | MgCl$_2$ | 60 | 2 |
| Sample of the Invention | 4 | 15 | 100 | 5 | NaOH | 10 | 90 | 2 | NaOH | 6.4 | None | | |
| Sample of the Invention | 5 | 30 | 98 | 3 | KOH | 10 | 90 | 2 | KOH | 5.0 | None | | |
| Comparative Sample | 6 | 35 | 45 | 5 | NaOH | 10 | 90 | 2 | NaOH | 5.5 | Ca(NO$_3$)$_2$ | 60 | 2 |
| Comparative Sample | 7 | 35 | 105 | 3 | NaOH | 5 | 80 | 2 | NaOH | 6.0 | Ca(NO$_3$)$_2$ | 60 | 2 |
| Comparative Sample | 8 | 35 | 125 | 3 | NaOH | 10 | 105 | 2 | None | | None | | |
| Comparative Sample | 9 | 35 | 98 | 2 | NaOH | 10 | 90 | 2 | None | | None | | |

TABLE 2

| Example | Fiber Sample No. | Increase in Nitrogen Content (%) | Amount of Carboxyl Groups (mmol/g) | Type of Metal of Carboxylate Groups | Molar Ratio of Free Carboxyl Groups to All Carboxyl Groups (%) | Gas Absorption after 2 Hours (%) | | | | pH of Fiber Dipped in Water | Tensile Strength g/d | pH-Buffering Ability | |
|---|---|---|---|---|---|---|---|---|---|---|---|---|---|
| | | | | | | Ammonia 100 ppm | Trimethyl-amine 100 ppm | Acetic Acid 50 ppm | Butyric Acid 50 ppm | | | Acid | Alkali |
| Sample of the Invention | 1 | 5.0 | 5.3 | Ca | 51 | 99 | 89 | 95 | 89 | 6.3 | 1.7 | 1300 | 300 |
| Sample of the Invention | 2 | 5.5 | 4.8 | Ca | 71 | 91 | 78 | 75 | 73 | 5.9 | 1.8 | 1000 | 320 |
| Sample of the Invention | 3 | 4.3 | 5.9 | Mg | 55 | 99 | 85 | 88 | 81 | 6.6 | 2.0 | 700 | 600 |
| Sample of the Invention | 4 | 3.5 | 6.2 | Na | 29 | 94 | 81 | 97 | 91 | 7.0 | 1.6 | 500 | 350 |

TABLE 2-continued

| Example | Fiber Sample No. | Increase in Nitrogen Content (%) | Amount of Carboxyl Groups (mmol/g) | Type of Metal of Metal Carboxylate | Molar Ratio of Free Carboxyl Groups to All Carboxyl Groups (%) | Gas Absorption after 2 Hours (%) | | | | pH of Fiber Dipped in Water | Tensile Strength g/d | pH-Buffering Ability | |
|---|---|---|---|---|---|---|---|---|---|---|---|---|---|
| | | | | | | Ammonia 100 ppm | Trimethyl-amine 100 ppm | Acetic Acid 50 ppm | Butyric Acid 50 ppm | | | Acid | Alkali |
| Sample of the Invention | 5 | 7.4 | 4.5 | K | 80 | 100 | 91 | 72 | 68 | 5.6 | 1.8 | 350 | 520 |
| Comparative Sample | 6 | 0.7 | 6.0 | Ca | 40 | 96 | 76 | 85 | 70 | 5.8 | 0.6 | 610 | 320 |
| Comparative Sample | 7 | 4.2 | 1.7 | Ca | 34 | 55 | 40 | 54 | 46 | 6.0 | 1.5 | 100 | 200 |
| Comparative Sample | 8 | 8.3 | 1.9 | Na | 98 | 63 | 51 | 52 | 39 | 5.1 | 1.5 | 50 | 300 |
| Comparative Sample | 9 | 5.0 | 5.2 | Na | 99 | 95 | 75 | 16 | 5 | 4.7 | 0.9 | 0 | 1100 |

Sample Nos. 1 to 5 of acidic or basic gas absorptive fiber of the present invention were found to have not only the ability to greatly absorb both acidic gas and basic gas, of which the properties are contradictory to each other, but also excellent fiber properties, and were found to be durable to post-processing such as carding. In addition, these were found to have excellent pH-buffering ability.

As opposed to these, the comparative sample No. 6, of which the increase in the nitrogen content resulting from the hydrazine treatment was small, was brittle as having a low tensile strength, though it had the ability to absorb acidic and basic gases. Therefore, this was not durable to post-processing such as carding. The comparative sample No. 7, which had been poorly hydrolyzed, and the comparative sample No. 8, which had been too much crosslinked, both had low ability to absorb acidic and basic gases, since the amount of carboxyl groups existing therein was small. The comparative sample No. 9, in which the ratio of the amount of free carboxyl groups to that of all carboxyl groups existing therein was high, had a low pH when dipped in water, and therefore had low ability to absorb acidic gas though having high ability to absorb basic gas.

EXAMPLE 2

10 parts of the fiber sample No. 1 of the invention that had been prepared in Example 1 was uniformly blended with 90 parts of acrylic fiber (Exlan K891-3d X V64) and spun into yarns having a yarn number count of 2/32 meters and a count of twist of 360 T/M, according to an ordinary method. These yarns were dyed and softened, using a Hank dyeing machine, then knitted according to an ordinary method using a circular rib pile knitting machine, and thereafter brushed, polished and sheared to give pile fabric having a pile length of 6 mm and a Metsuke weight of 400 g/m². On the other hand, 50 parts of the fiber sample No. 1 of the invention that had been prepared in Example 1 and 50 parts of hollow polyester fiber (3 d×51 mm) were pre-beaten in a fiber blender, and then formed into card web using a roller carder. Using the card web as the padding and the pile fabric as the cover, formed were stuffed samples.

Five-women panelists each used the sample for one month, who were required to answer questionnaires. They all answered that, while using the sample in a room, they were not worried about any odors in the room. In particular, the smoking panelists answered that the odor from their cigarettes was reduced in the room. These results may suggest the applicability of the fiber of the invention to the padding, for example, in bed kilts, pillows, cushions and sweat absorbers.

As has been described in detail hereinabove, it is worthy of special mention that the present invention has realized the industrial and advantageous provision of acidic or basic gas absorptive fiber having physical properties with no problem on the practical level. Even after having been saturated with gases absorbed, the gas absorptive fiber of the present invention can be easily restored to its original condition if it is exposed to clean air. Therefore, the fiber is applicable to cycle use. The acidic or basic gas absorptive fiber of the present invention is weakly acidic by itself, and therefore has pH-buffering ability, which is such that even when the fiber is attacked by any external acids or alkalis, it still maintain its pH to fall between 5 and 7. Moreover, since the fabric can be worked into various shapes of, for example, non-woven fabric, knitted fabric and woven fabric, it can be widely used in various fields that require absorption of acidic and basic gases. For example, the fiber of the invention can be used in ordinary clothing such as inner wear, underwear, lingerie, pajamas, baby goods, girdles, brassieres, socks, tights, leotards, trunks, etc.; inner or outer clothing such as sweaters, sweat shirts, suits, sportswear, scarves, handkerchiefs, mufflers, artificial leather, baby wear, etc.; cloth of bed kilts; padding in bed kilts, pillows, stuffed dolls and toys; bedding such as sheets, blankets, cushions, etc.; interior goods such as curtains, carpets, mats, wallpapers, stuffed goods, artificial flowers, artificial trees, etc.; sanitary goods such as masks, shorts for incontinence, wet tissue, etc.; car goods such as sheets, upholstery, etc.; toiletry goods such as toilet covers, toilet mats, pet toilets, etc.; lining in kitchenware such as refrigerators, garbage boxes, etc.; water-purifying elements such as filters for decorative fish tanks and fish cultivation tanks, filters for bathes, filters for drainage, etc.; air-conditioning elements such as filters for air conditioners, filters for air purifiers, air filters for clean rooms, filters for moisture-removers, filters for gas processors in industrial use; industrial materials such as fillers in gas-absorbing towers, etc.; and other various substances such as inner soles, slippers, gloves, towels, mops, linings in rubber gloves, inner soles in boots, adhesive materials, kitchen garbage processors, absorbents, supporters, sweat-absorbing pads, padding in clothes, etc.

The fiber of the present invention can be used singly and even in combination with any other fibers to be blended therewith and spun. The latter blend spun fibers may be used more effective in various fields such as those mentioned above. For example, where the fiber of the invention is desired to be used as padding in bed kilts or as non-woven fabric, it may be blended and spun with other fibers, such as polyester fiber, to give more bulky yarns. If the fiber of the invention is combined with any absorbents other than acidic or basic gas absorbents, it is possible to obtain more useful absorbents applicable to much more diversified objects. Thus, in order to make the fiber of the invention have additional functions, or in order to reduce the mixing ratio of the fiber in blended yarns, the fiber may be combined with various other materials. The fiber of the invention is also usable in ion-exchange substances to be applicable to, for example, water processors and metal adsorbents.

While the invention has been described in detail and with reference to specific embodiments thereof, it will be apparent to one skilled in the art that various changes and modifications can be made therein without departing from the spirit and scope thereof.

What is claimed is:

1. A fiber having both a degree of acidic gas absorption, as measured according to the following test method I, of 70% or higher, and a degree of basic gas absorption, as measured according to the following test method II, of 80% or higher.

Test Method I

One gram of the fiber as dried absolutely at 105° C. is left in a standard atmosphere at 20° C. and at 65% RH for 10 hours or longer, then airtightly sealed in a Tedlar® bag along with 1000 ml of a mixed gas comprising air and having an acetic acid concentration of 50 ppm, and left therein at 20° C. for 2 hours; and the acetic acid concentration in the mixed gas in the bag is measured, from which is obtained the decrease in acetic acid gas therein that indicates the degree of acidic gas absorption of the fiber.

Test Method II

One gram of a fiber sample as dried absolutely at 105° C. is left in a standard atmosphere at 20° C. and at 65% RH for 10 hours or longer, then airtightly sealed in a Tedlar® bag along with 1000 ml of a mixed gas comprising air and having an ammonia concentration of 100 ppm, and left therein at 20° C. for 2 hours; and the ammonia concentration in the mixed gas in the bag is measured, from which is obtained the decrease in ammonia gas therein that indicates the degree of basic gas absorption of the fiber.

2. The fiber as claimed in claim 1, which is crosslinked acrylic fiber, of which the increase in the nitrogen content resulting from hydrazine crosslinking therein falls between 1.0 and 8.0% by weight, which has from 2.5 to 6.0 mmol/g of carboxyl groups as introduced into a part of the remaining nitrile groups while having amido groups as introduced into the remaining part thereof, and in which a part of said carboxyl groups are of salt types with one or more metals selected from K, Na, Ca, Mg and Al while the proportion of the amount of free carboxyl groups to the amount of all said carboxyl groups falls between 30 and 95 mol %.

3. The fiber as claimed in claim 1, which has, when dispersed in water in an amount of one gram per 500 ml of water, an equilibrated pH of from 5.0 to 8.0.

4. Acidic or basic gas absorptive fabric, which comprises acidic or basic gas absorptive fiber of claim 1, in an amount of 5% by weight or more.

5. The fiber as claimed in claim 2, which has, when dispersed in water in an amount of one gram per 500 ml of water, an equilibrated pH of from 5.0 to 8.0.

6. Acidic or basic gas absorptive fabric, which comprises acidic or basic gas absorptive fiber of claim 2, in an amount of 5% by weight or more.

7. Acidic or basic gas absorptive fabric, which comprises acidic or basic gas absorptive fiber of claim 3, in an amount of 5% by weight or more.

8. Acidic or basic gas absorptive fabric, which comprises acidic or basic gas absorptive fiber of claim 5, in an amount of 5% by weight or more.

9. A fabric which comprises, in an amount of 5% by weight or more, fiber having both a degree of acidic gas absorption, as measured according to the following test method I, of 70% or higher, and a degree of basic gas absorption, as measured according to the following test method II, of 80% or higher.

Test Method I

One gram of the fiber as dried absolutely at 105° C. is left in a standard atmosphere at 20° C. and at 65% RH for 10 hours of longer, then airtightly sealed in a Tedlar® bag along with 1000 ml of a mixed gas comprising air and having an acetic acid concentration of 50 ppm, and left therein at 20° C. for 2 hours; and the acetic acid concentration in the mixed gas in the bag is measured, from which is obtained the decrease in acetic acid gas therein that indicates the degree of acidic gas absorption of the fiber.

Test Method II

One gram of the fiber as dried absolutely at 105° C. is left in a standard atmosphere at 20° C. and at 65% RH for 10 hours or longer, then airtightly sealed in a Tedlar® bag along with 1000 ml of a mixed gas comprising air and having an ammonia concentration of 100 ppm, and left therein at 20° C. for 2 hours; and the ammonia concentration in the mixed gas in the bag is measured, from which is obtained the decrease in ammonia gas therein that indicates the degree of basic gas absorption of the fiber.

10. The fabric as claimed in claim 9, wherein the fiber is crosslinked acrylic fiber, of which the increase in the nitrogen content resulting from hydrazine crosslinking therein falls between 1.0 and 8.0% by weight, which has from 2.5 to 6.0 mmol/g of carboxyl groups as introduced into a part of the remaining nitrile groups while having amido groups as introduced into the remaining part thereof, and in which a part of said carboxyl groups are of salt types with one or more metals selected from K, Na, Ca, Mg and Al while the proportion of the amount of free carboxyl groups to the amount of all said carboxyl groups falls between 30 and 95 mol %.

11. The fabric as claimed in claim 9, wherein the fiber has, when dispersed in water in an amount of one gram per 500 ml of water, an equilibrated pH of from 5.0 to 8.0.

12. The fabric as claimed in claim 10, wherein the fiber has, when dispersed in water in an amount of one gram per 500 ml of water, an equilibrated pH of from 5.0 to 8.0.

* * * * *